US00PP28642P3

(12) United States Plant Patent
Kobayashi

(10) Patent No.: US PP28,642 P3
(45) Date of Patent: Nov. 14, 2017

(54) POINSETTIA PLANT NAMED 'PER6115'

(50) Latin Name: ***Euphorbia pulcherrima* Willd.**
Varietal Denomination: PER6115

(71) Applicant: Ruth Kobayashi, Carlsbad, CA (US)

(72) Inventor: Ruth Kobayashi, Carlsbad, CA (US)

(73) Assignee: Dümmen Group B.V., De Lier (NL)

( * ) Notice: Subject to any disclaimer, the term of this patent is extended or adjusted under 35 U.S.C. 154(b) by 120 days.

(21) Appl. No.: 14/757,313

(22) Filed: Dec. 15, 2015

(65) Prior Publication Data

US 2017/0071089 P1 Mar. 9, 2017

Related U.S. Application Data

(60) Provisional application No. 62/283,673, filed on Sep. 5, 2015.

(51) Int. Cl.
*A01H 5/02* (2006.01)

(52) U.S. Cl.
USPC ..... Plt./307

(58) Field of Classification Search
USPC ..... Plt./263.1, 302, 303, 307
See application file for complete search history.

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of Poinsettia plant named 'PER6115', characterized by its uniform, upright and mounded plant habit; moderately vigorous growth habit; freely and upright to somewhat outwardly branching habit; dark green-colored leaves; under natural season conditions, plants flower on or about November 16 in Southern California; large inflorescences with smooth and bright red-colored flower bracts; and good post-production longevity.

2 Drawing Sheets

Botanical designation: *Euphorbia pulcherrima* Willd.
Cultivar denomination: 'PER6115'.

BACKGROUND OF THE INVENTION

The present invention relates to a new and distinct cultivar of Poinsettia plant, botanically known as *Euphorbia pulcherrima* Willd., and hereinafter referred to by the cultivar name 'PER6115'.

The new Poinsettia plant is a product of a planned breeding program conducted by the Inventor in Encinitas, Calif. The objective of the breeding program is to create new uniform Poinsettia plants having large inflorescences with attractive flower bracts and excellent post-production longevity.

The new Poinsettia plant is a naturally-occurring whole plant mutation of *Euphorbia pulcherrima* Willd. '490', disclosed in U.S. Plant Pat. No. 7,825. The new Poinsettia plant was discovered and selected by the Inventor as a single flowering plant from within a population of plants of '490' in a controlled greenhouse environment in Encinitas, Calif. in December, 2014.

Asexual reproduction of the new Poinsettia plant by terminal vegetative cuttings in a controlled greenhouse environment in Encinitas, Calif. since January, 2015 has shown that the unique features of this new Poinsettia plant are stable and reproduced true to type in successive generations of asexual reproduction.

SUMMARY OF THE INVENTION

Plants of the new Poinsettia have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'PER6115'. These characteristics in combination distinguish 'PER6115' as a new and distinct Poinsettia plant:

1. Uniform, upright and mounded plant habit.
2. Moderately vigorous growth habit.
3. Freely and upright to somewhat outwardly branching habit.
4. Dark green-colored leaves.
5. Under natural season conditions, plants flower on or about November 16 in Southern California.
6. Large inflorescences with smooth and bright red-colored flower bracts.
7. Good post-production longevity.

In side-by-side comparisons conducted in Encinitas, Calif., plants of the new Poinsettia differ primarily from plants of '490' in the following characteristics:

1. Plants of the new Poinsettia flower about one week earlier than plants of '490' when grown under natural season conditions in Southern California.
2. Plants of the new Poinsettia and '490' differ in flower bract color as plants of '490' have dark red-colored flower bracts.

Plants of the new Poinsettia can be compared to plants of the *Euphorbia pulcherrima* Willd. 'Peterstar', disclosed in U.S. Plant Pat. No. 8,259. In side-by-side comparisons conducted in Encinitas, Calif., plants of the new Poinsettia differed primarily from plants of 'Peterstar' in the following characteristics:

1. Plants of the new Poinsettia were more vigorous than plants of 'Peterstar'.

2. Plants of the new Poinsettia had darker green-colored leaves than plants of 'Peterstar'.
3. Plants of the new Poinsettia and 'Peterstar' differed in flower bract color and texture as plants of 'Peterstar' had orange red-colored flower bracts that were slightly rugose.

Plants of the new Poinsettia can also be compared to plants of the *Euphorbia pulcherrima* Willd. 'PER2804', disclosed in U.S. Plant Pat. No. 19,295. In side-by-side comparisons conducted in Encinitas, Calif., plants of the new Poinsettia differed primarily from plants of 'PER2804' in the following characteristics:

1. Plants of the new Poinsettia had darker green-colored leaves than plants of 'PER2804'.
2. Plants of the new Poinsettia and 'PER2804' differed in flower bract size and color as plants of 'PER2804' had smaller and lighter red-colored flower bracts.
3. Plants of the new Poinsettia flowered about two weeks later than plants of 'PER2804' when grown under natural season conditions in Southern California.

BRIEF DESCRIPTION OF THE PHOTOGRAPHS

The accompanying photographs illustrate the overall appearance of the new Poinsettia plant showing the colors as true as it is reasonably possible to obtain in colored reproductions of this type. Colors in the photographs may differ slightly from the color values cited in the detailed botanical description which accurately describe the colors of the new Poinsettia plant.

The photograph on the first sheet is a side perspective view of a typical flowering plant of 'PER6115'.

The photograph on the second sheet is a close-up view of a typical flowering plant of 'PER6115'.

DETAILED BOTANICAL DESCRIPTION

Plants used in the aforementioned photographs and in the following detailed description were grown during the late autumn/early winter in 16.5-cm containers in a polyethylene-covered greenhouse in Encinitas, Calif. and under natural season conditions and cultural practices typical of commercial Poinsettia production. During the production of the plants, day temperatures averaged 26° C., night temperatures averaged 18° C. and light levels averaged 5,000 foot-candles. Measurements and numerical values represent averages for typical flowering plants. Plants were pinched one time and were 21 weeks old when the photographs and the description were taken. In the following description, color references are made to The Royal Horticultural Society Colour Chart, 2007 Edition, except where general terms of ordinary dictionary significance are used.

Botanical classification: *Euphorbia pulcherrima* Willd. 'PER6115'.

Parentage: Naturally-occurring whole plant mutation of *Euphorbia pulcherrima* Willd. '490', disclosed in U.S. Plant Pat. No. 7,825.

Propagation:

*Type.*—Terminal vegetative cuttings.

*Time to initiate roots.*—About five to seven days at night temperatures about 20° C. and day temperatures about 27° C.

*Time to produce a rooted young plant.*—About four weeks at night temperatures about 20° C. and day temperatures about 27° C.

*Root description.*—Fibrous; typically white in color, actual color of the roots is dependent on substrate composition, water quality, fertilizer type and formulation, substrate temperature and physiological age of roots.

Plant description:

*Plant habit and form.*—Uniform, upright and mounded plant habit; inverted triangle; large inflorescences positioned above the foliar plane; moderately vigorous growth habit.

*Plant height.*—About 33 cm.

*Plant diameter or spread.*—About 52 cm.

*Lateral branch description.*—Quantity: Freely branching habit, about seven lateral branches develop after pinching. Length: About 29 cm. Diameter: About 7 mm. Internode length: About 2.3 cm. Strength: Strong. Texture: Smooth, glabrous. Luster: Glossy. Color: Close to 146A.

*Leaf description.*—Arrangement: Alternate, simple. Length: About 11.25 cm. Width: About 8.1 cm. Shape: Ovate. Apex: Acuminate. Base: Nearly truncate. Margin: Entire with shallow crenations; slightly undulate Aspect: Flat to keeled. Venation pattern: Pinnate, arcuate. Texture, upper surface: Smooth, glabrous; velvety. Texture, lower surface: Smooth, glabrous; prominent venation. Luster, upper and lower surfaces: Dull. Color: Developing leaves, upper surface: Darker than 147A. Developing leaves, lower surface: Close to 137A. Fully expanded leaves, upper surface: Darker than 147A; venation, close to 146A to 146B tinged with close to 187A to 187B. Fully expanded leaves, lower surface: Close to 137B; venation, close to 146B to 146C tinged with close to 187B. Petioles: Length: About 4.5 cm. Diameter: About 3.5 mm. Texture, upper and lower surfaces: Smooth, glabrous. Luster, upper and lower surfaces: Glossy. Color, upper surface: Close to 187B. Color, lower surface: Close to 183B.

Inflorescence description:

*Inflorescence type and habit.*—Terminal inflorescences are compound corymbs of cyathia with colored flower bracts subtending the cyathia; inflorescences uniformly positioned above the foliar plane.

*Fragrance.*—None detected.

*Flowering response.*—Early season flowering response; under natural season conditions, plants typically flower in mid-November in Southern California; under artificial long nyctoperiod/short photoperiod conditions, plants flower within about eight weeks.

*Post-production longevity.*—Good post-production longevity; plants of the new Poinsettia maintain good substance and flower bract color for about four weeks under interior conditions; inflorescences persistent.

*Inflorescence diameter.*—About 33 cm.

*Inflorescence height (depth).*—About 4.5 cm.

*Flower bracts.*—Quantity per inflorescence: About 18. Length, largest bracts: About 15.4 cm. Width, largest bracts: About 11.2 cm. Shape: Ovate. Apex: Acuminate. Base: Obtuse or truncate. Margin: Entire with shallow crenations; slightly undulate. Aspect: Flat to keeled. Venation pattern: Pinnate, arcuate. Texture, upper surface: Smooth, glabrous; velvety. Texture, lower surface: Smooth, glabrous; prominent venation. Luster, upper and lower surfaces: Dull. Color: Developing or transitional bracts, upper surface: Towards the margins, random sectors, close to 53C; towards the center, random sectors, close to 147A. Developing or transitional bracts, lower surface: Towards the margins, random sectors, close to 58A; towards the center, random sectors, close to 137A and 137B. Fully expanded bracts, upper surface: Darker than 46A; venation, close to 53A; color does not change with development. Fully expanded bracts, lower surface: Close to 46A; venation, close to 53B to 53C; color does not fade with development. Bract petioles: Length: About 3.5 cm. Diameter: About 3 mm. Texture, upper and lower surfaces: Smooth, glabrous. Luster, upper and lower surfaces: Glossy. Color, upper and lower surfaces: Close to 185A.

*Cyathia.*—Quantity per corymb: About nine to twelve. Length: About 1 cm. Width: About 6 mm. Shape: Ovoid. Texture: Smooth, glabrous. Color, immature: Close to 146A. Color, mature: Close to 146A to 146B.

*Nectaries.*—Quantity per cyathium: Typically one. Length: About 6 mm. Width: About 4.5 mm. Shape: Elliptical. Texture: Smooth, glabrous. Color: Close to 15A to 15B.

*Peduncles.*—Length: About 4 mm. Diameter: About 2 mm. Strength: Strong. Aspect: Mostly upright to slightly outwardly. Texture: Smooth, glabrous. Color: Close to 146B.

*Reproductive organs.*—Stamens: Quantity per cyathium: About 12 to 16. Filament length: About 3.5 mm. Filament color: Close to 59A. Anther shape: Oval; bi-lobed. Anther length: Less than 1 mm. Anther color: Close to 59A. Amount of pollen: Scarce to moderate. Pollen color: Close to 12A. Pistils: Pistil development has not been observed on plants of the new Poinsettia.

*Seeds and fruits.*—Seed and fruit production have not been observed on plants of the new Poinsettia.

Disease & pest resistance: Plants of the new Poinsettia have not been shown to be resistant to pathogens and pests common to Poinsettia plants.

Temperature tolerance: Plants of the new Poinsettia have been observed to tolerate temperatures ranging from about 16° C. to about 29° C.

It is claimed:

1. A new and distinct Poinsettia plant named 'PER6115' as illustrated and described.

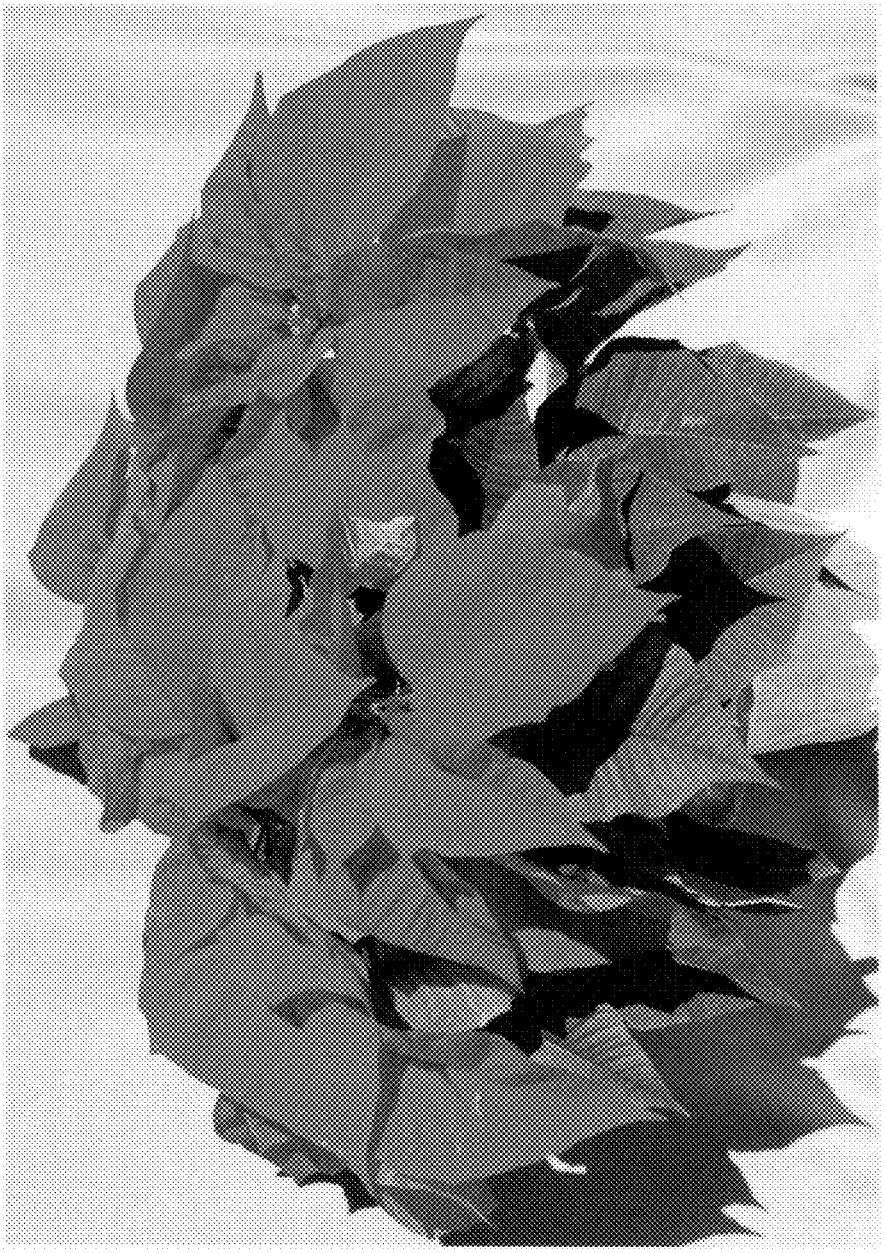

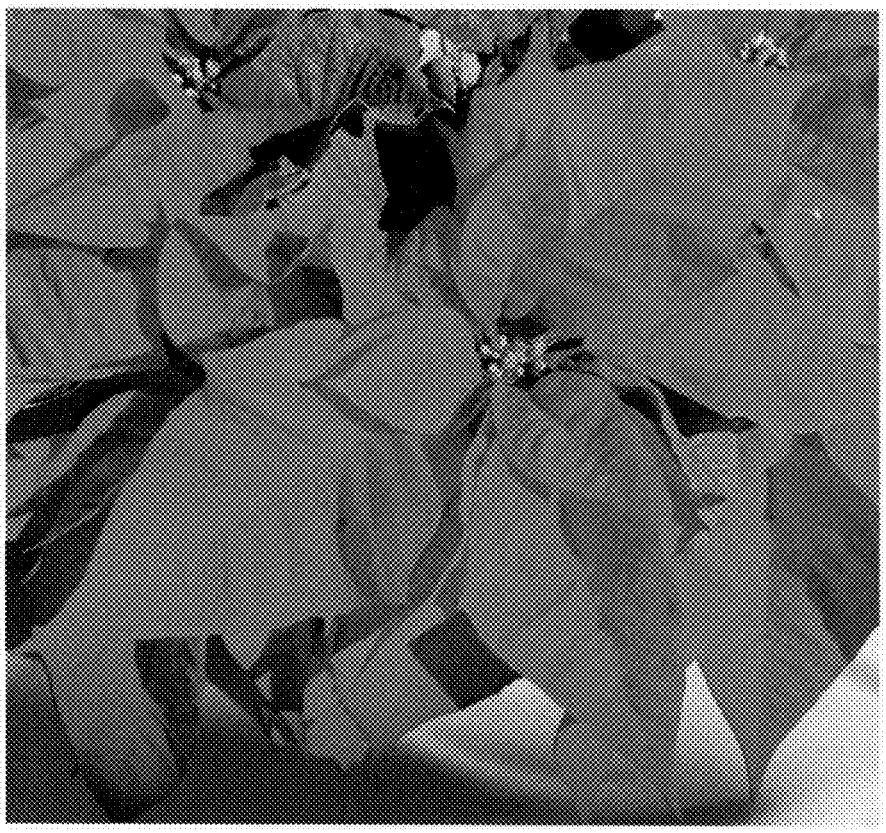

* * * * *